(12) United States Patent
Höglund

(10) Patent No.: US 8,696,692 B2
(45) Date of Patent: Apr. 15, 2014

(54) TISSUE LIGATION DEVICE

(75) Inventor: Odd Höglund, Knivsta (SE)

(73) Assignee: Vetok AB, Knivsta (SE)

( * ) Notice: Subject to any disclaimer, the term of this patent is extended or adjusted under 35 U.S.C. 154(b) by 356 days.

(21) Appl. No.: 12/811,059

(22) PCT Filed: Dec. 30, 2008

(86) PCT No.: PCT/SE2008/051572
§ 371 (c)(1),
(2), (4) Date: Jun. 28, 2010

(87) PCT Pub. No.: WO2009/091313
PCT Pub. Date: Jul. 23, 2009

(65) Prior Publication Data
US 2010/0292793 A1    Nov. 18, 2010

(30) Foreign Application Priority Data

Jan. 14, 2008 (SE) ........................................ 0800082

(51) Int. Cl.
*A61B 17/08* (2006.01)
(52) U.S. Cl.
USPC .......................................................... 606/151

(58) Field of Classification Search
USPC .............. 24/16 PB, 17 A, 17 AP, 30.5 P, 306, 24/712.1, 712.2; 606/151, 157, 158
See application file for complete search history.

(56) References Cited

U.S. PATENT DOCUMENTS

| 3,102,311 | A | * | 9/1963 | Martin et al. ................ | 24/16 PB |
| 4,001,898 | A | * | 1/1977 | Caveney ...................... | 24/16 PB |
| 4,183,119 | A |   | 1/1980 | Stewart et al. | |
| 4,955,913 | A |   | 9/1990 | Robinson | |
| 6,105,210 | A | * | 8/2000 | Benoit ......................... | 24/16 PB |
| 2006/0123603 | A1 | * | 6/2006 | Hewes ......................... | 24/16 PB |
| 2007/0016230 | A1 | * | 1/2007 | Jambor et al. ................ | 606/157 |
| 2009/0270923 | A1 | * | 10/2009 | Tormala et al. .............. | 606/263 |

* cited by examiner

*Primary Examiner* — Ashley Fishback
(74) *Attorney, Agent, or Firm* — Birch, Stewart, Kolasch & Birch, LLP

(57) ABSTRACT

A medical device comprises an elongated, flexible band equipped with ratchet members and connected to a device head having a channel dimensioned for reception of the band. A lock member is connected to the head and configured to interlock the ratchet members when the band is pulled through the channel to form a reverse-motion brake. A protrusion and a matching protrusion receiving member are arranged in the head in connection with the channel entrance and in the band in connection with the band-head interface. The protrusion receiving member is dimensioned for reception of the protrusion when the band is close to fully pushed into the head.

19 Claims, 6 Drawing Sheets

TISSUE LIGATION DEVICE

TECHNICAL FIELD

The present invention generally relates to medical devices, and in particular to tissue ligation devices.

BACKGROUND

Ligation is the medical act of restricting blood flow in a blood vessel or other tissue. Traditionally, tissue ligation is conducted using a ligature usually in the form of a thread or string, tied around the tissue. Other prior art ligation devices include metal clips that are pinched around the tissue.

Even though the ligature is a very simple device, the act of tissue ligation can be very cumbersome, sometimes requiring the operation of more than one medical person. For instance, in some surgical operations the tissue to become ligated needs to be lifted slightly from surrounding tissue in a subject. However, tying the ligature thread around the lifted tissue typically requires two hands, in particular when pulling the thread tightly around the tissue and locking the thread with a knot. In these cases, some other medical person then has to lift the tissue from the surroundings or withdraw the surrounding tissue.

There is therefore a need for a medical device that has the potential of being used for tissue ligation and can be operated with one hand.

Metal clips have the disadvantage of requiring a further operation or surgical procedure for later removing the clips.

US 2005/0288674 discloses a bio-absorbable bone tie having a convex head and an elongated band used for securing fragments of a fractured bone together. The bone tie is basically constructed as a traditional cable tie with the exception of the convex head.

SUMMARY

The present invention overcomes these and other drawbacks of the prior art arrangements.

It is a general objective to provide a medical device suitable for tissue ligation.

It is another objective to provide a tissue ligation device that can be handled in a single hand operation.

Yet another objective is to provide a medical device suitable for ligation of even very thin tissues.

These and other objectives are met by embodiments as defined by the accompanying patent claims.

Briefly, the present embodiments involve a medical device suitable for tissue ligation. The device comprises an elongated, flexible band equipped with ratchet members along at least a trailing band portion. A device head is connected to the trailing end of the band and has a channel dimensioned for reception of a leading end of the band. A lock member is connected to the device head and is disposed in connection with the channel. The lock member comprises at least one lock tooth configured to interlock ratchet members in the band when the band is being pulled through the channel. The lock member and the ratchet member mutually engage for allowing a forward movement of the band through the channel but restrain any backward band movement relative the head similarly to a reverse-motion brake of a cable tie.

In an embodiment, a protrusion is provided in the device head in connection with the band entrance to the channel. The band comprises a matching protrusion receiving member in connection with its trailing end. Alternatively, the protrusion is arranged in the band on its trailing end with the matching protrusion receiving member present in the device head, preferably in one of its inner walls. In either case, the receiving member is dimensioned for reception of the protrusion when the band is fed into the channel. The protrusion and receiving member significantly reduce the band loop diameter when the band is fully pulled through the channel in the device head and can even achieve zero loop diameters. This is an important feature for tissue ligation, especially when handling very thin tissues, such as blood vessels in animals, including humans. The protrusion has the further advantage in addition to reducing the loop diameter in that it has tissue engaging properties for reducing the risk that the medical device slips along the tissue during and after tissue ligation.

The device head preferably comprises at least one tissue engaging member that comprises elements that can grip into the tissue during and after ligation to thereby prevent the medical device from slipping along the tissue during and after the procedure, respectively.

An intermediate portion of the band is preferably U-shaped to thereby align the leading band end close to the device head. This further simplifies introducing the leading end into the head channel using a single hand of the operator.

In a preferred embodiment, the medical device is made of a resorbable material to be gradually degraded or dissolved after the ligation procedure, thereby relaxing the need for a further surgical operation to remove the medical device after tissue healing.

Embodiments offer the following advantages:
Enables ligation of tissue and vessels with one hand;
Reduces the risk of the ligature slipping off the tissue;
Can be used for ligation of very thin tissues; and
Can be made fully absorbable or resorbable.

Other advantages offered by the embodiments will be appreciated upon reading of the below detailed description.

SHORT DESCRIPTION OF THE DRAWINGS

The invention together with further objects and advantages thereof, may best be understood by making reference to the following description taken together with the accompanying drawings, in which.

DETAILED DESCRIPTION

Figure 1:
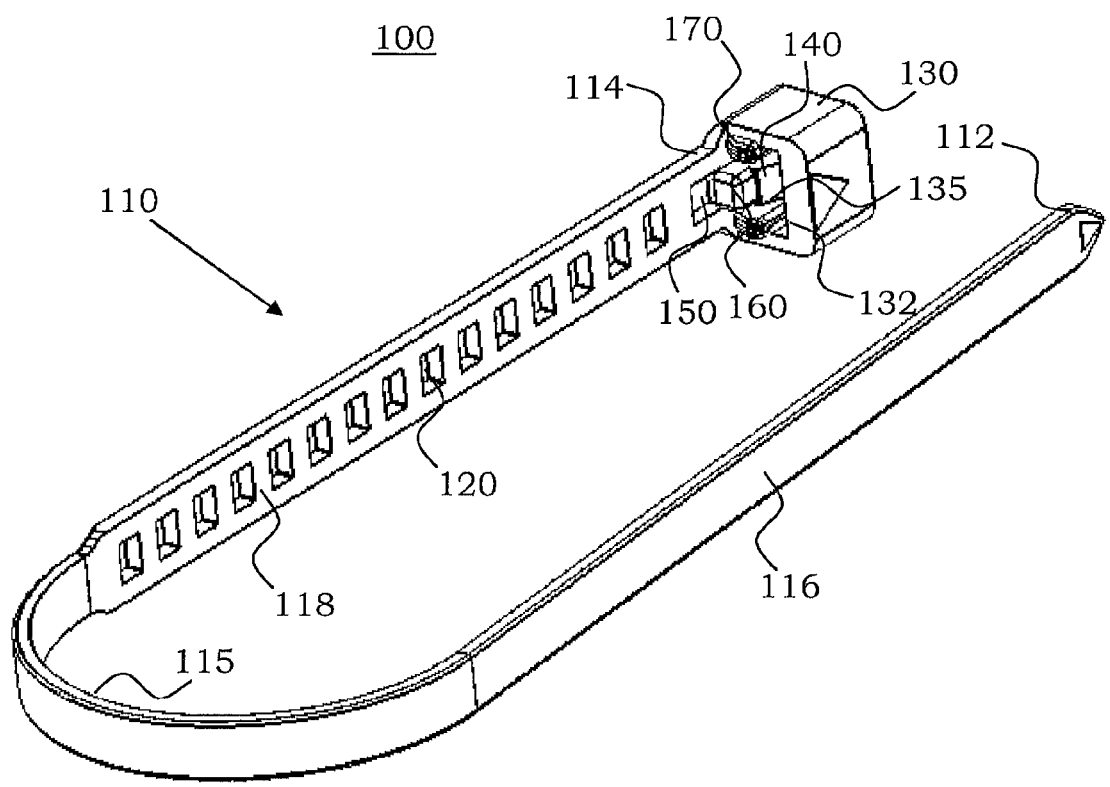
FIG. 1 is an illustration of a medical device according to an embodiment of the present invention.

Throughout the drawings, the same reference characters will be used for corresponding or similar elements.

The present invention relates to a medical device suitable for ligation of tissues and vessels in an animal body, such as a mammalian body, including a human body, and to a method of using such a device in performing tissue ligation.

The improved medical device, ligature, of the invention has significant advantages over the prior art thread-based ligatures. Firstly, the medical device can be handled by one hand of a medical person, leaving the other hand free for lifting the tissue to be ligated slightly out from the surrounding body. Furthermore, the locking of the medical device is simplified and does not require tying any knots in the limited space where the surgical operation is taking place in the animal or human body.

The medical device of the present invention is based on the principles of a cable tie (also denoted strap, zip tie, mouse belt, tie wrap, tie rap and quick draw in the art) for allowing forward motion of a band relative a lock member but restricting or even fully preventing backward movement of the band relative the lock member. This feature of cable tie, providing a reverse-motion brake, replaces the cumbersome operation of tying knots of thread ligatures and thereby significantly simplifies the ligation process.

FIG. 1 is an illustration of a particular embodiment of a medical device 100 according to the present invention suitable for tissue ligation. The medical device 100 comprises an elongated, flexible band or strip 110 having a front side 118 and an opposite rear side 116. A trailing end 114 of the band 110 is attached and anchored to a head 130 of the medical device 100. The opposite leading band end 112 is adapted for insertion into a channel 135 running through the device head 130.

The leading band end 112 can be pointed for facilitating guiding of the band 110 into the head channel 135. The end 112 could even be sharp to be able to penetrate tissue, when such a function is required.

The reverse-motion braking action of the invention is achieved through ratchet members 120 provided in at least a portion of the band 110. The ratchet members 120 are preferably arranged on at least the front side 118 of the band 110 but could also, or instead, be present on the rear side 116 as is illustrated in the figure.

The ratchet members 120 are arranged on at least the portion of the band 110 that is closest to the trailing end 114 and the device head 130. As a consequence, the ratchets 120 can start at the trailing end 114 or close to the trailing end 114 and run at least a distance up through the band length towards the leading end 112. It is actually possible to have ratchet members 120 along the whole length of the band 110 but for most practical applications it is adequate to have the ratcheting 120 up to a sub-part of the band lengths. In this context, the important feature regarding the ratcheting length is that the ratchet members 120 should be provided at least up to a portion of the band length towards the leading end 112 to engage a lock member 140 in the device head 130 when the leading end 112 is fed into the channel 135 and the band 110 forms a loop around a tissue to be ligated. Thus, the largest diameter of the loop when the lock member 140 first starts engaging with the ratchet members 120 as the leading band end 112 is pulled through the channel 135 should preferably be larger than the outer diameter of the tissue present in the loop. For most practical applications, the ratcheting 120 could therefore be from about one or few centimeters up to several centimeters.

The ratchet members 120 can, in a first embodiment, be realized as an array of holes or apertures through the band 110 as illustrated in the figure. These holes form, together with the intermediate band material, a ladder structure that can be engaged by the lock member 140 in the device head 130 to achieve the reverse-motion brake. In a second embodiment, the ratchet members 120 are instead a plurality of notches in the front side 118 or the rear side 116 of the band 110. These notches, thus, form indentations in the band 110 but not necessarily penetrate through the whole thickness of the band 110 as in the first embodiment. A third ratcheting embodiment is to replace the holes or notches with a plurality of protruding members, such as ratchet teeth that extend a short distance from the front or rear side surface.

The device head 130 comprises the lock member 140 disposed in connection with the channel 135, which is running through the head 130 and is dimensioned for reception of the band 110. The lock member 140 comprises at least one lock tooth or latching element 145 dimensioned to interlock ratchet members 120 defined in the band 110. In the case of hole- or notch-implemented ratchet members 120, the locking tooth 145 is arranged for step-by-step protrusion into the holes or notches as the band 110 is being fed through the channel 135. Correspondingly, the locking tooth 145 engages with the protrusion of a ratchet teeth solution as the band 110 is being pulled through the channel 135 in the head 130.

The inter-engagement between the lock member 140 and the ratchet member 120 permits forward movement of the band 110 through the channel 135 but restrains the band 110 against reverse movement through the channel 135, thereby achieving a reverse-motion brake.

Figure 2:
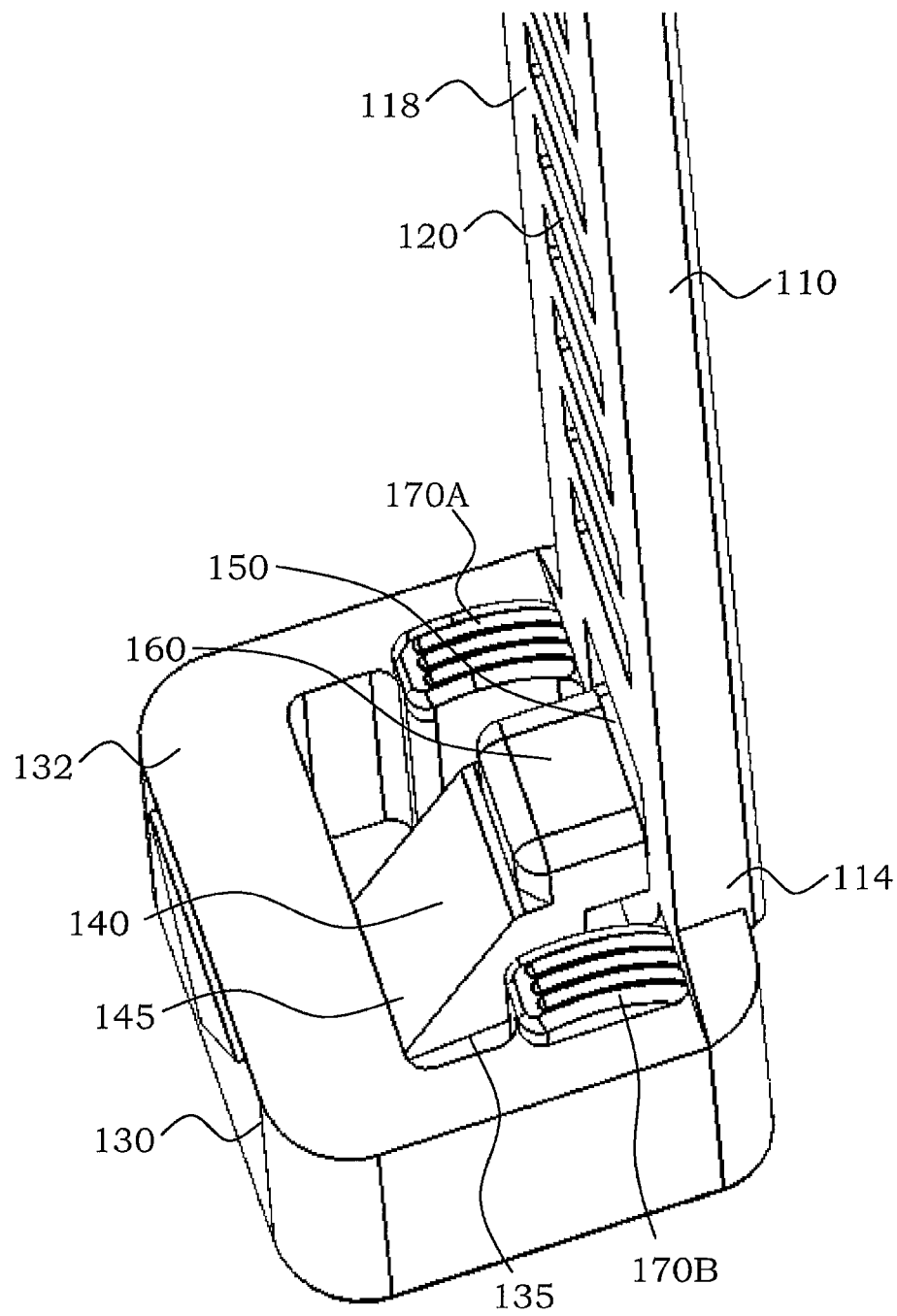
FIG. 2 is a magnification of the device head in the medical device of FIG. 1 from a first view.
Figure 3:
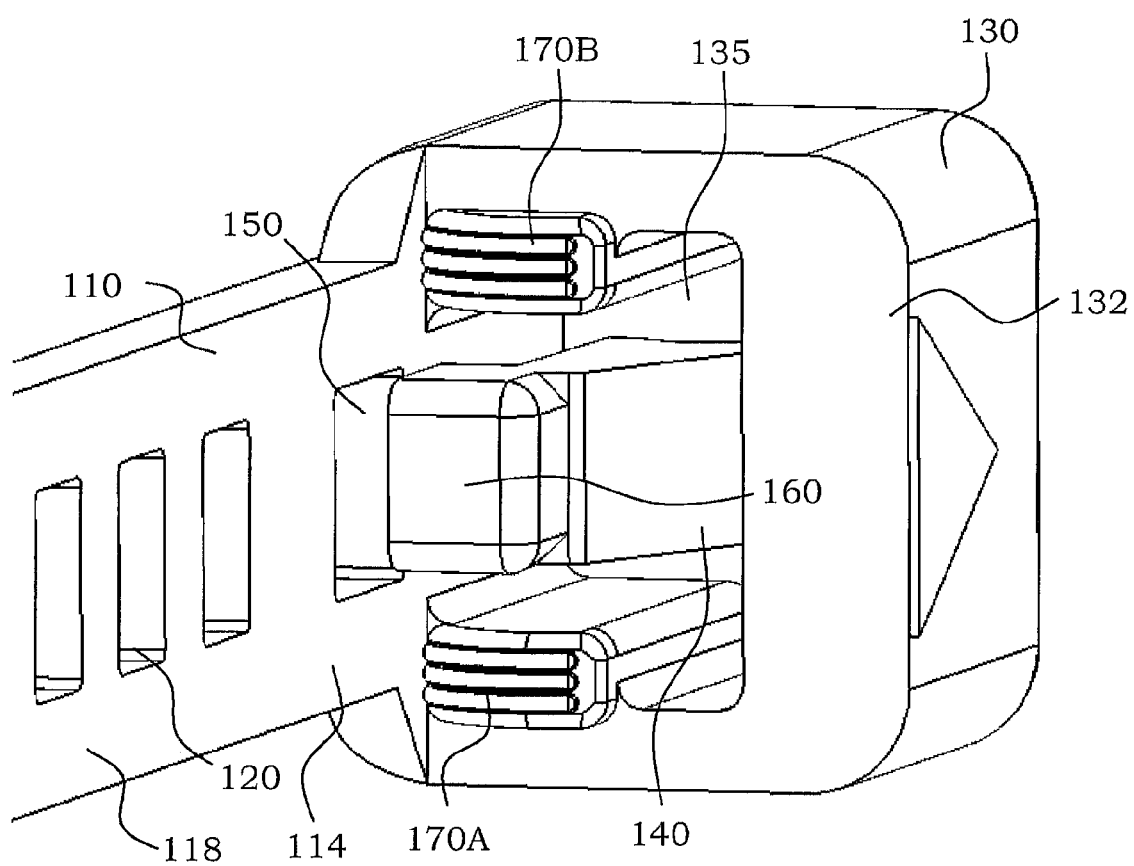
FIG. 3 is a magnification of the device head in the medical device of FIG. 1 from a second view.

The locking tooth 145 of the lock member 140 is more clearly shown in FIGS. 2 and 3. As is seen in these figures, the tooth 145 preferably ramps upward from the entrance side to the exit side of the channel 135, while the opposite face of the tooth drops vertically. It is anticipated by the present invention that the lock member 140 may include multiple locking teeth 145, such as positioned in series or as a train in connection with, preferably in, the head channel 130.

The lock member 140 is disposed in connection with the channel 135 and is preferably, as is illustrated in FIGS. 1 to 3, provided somewhere along the length of the channel 135. Alternatively or in addition, the lock member 140 could be provided in connection with the entrance and/or exit of the channel 135 in the device head 130.

The lock member 140 can be situated in connection with the inner wall of the device head 130 that is on the same side of the channel 135 as the band 110. The ratchet members 120 are then provided on at least the front side of the band 110. Alternatively, the lock member 140 is provided on the inner wall opposite the side of the channel 135 at which the band 110 is anchored to the device head 130. The ratchet members 120 are therefore provided on at least the rear side 116 of the band 110.

The medical device 100 of the present invention also comprises a protrusion 160 arranged, in this embodiment, in the device head 130 in connection with the entrance to the channel 135. A matching protrusion receiving member 150 is provided in the band 110 in connection with the trailing end 114. The receiving member 150 is dimensioned for allowing reception of the protrusion 160.

The protrusion 160 is preferably arranged on the same side of the channel 135 in the device head 130 as the trailing end 114 is connected to the head 130. Correspondingly, the receiving member 150 is preferably arranged in the portion of the band 110 that is in the interface or next to the transition between the band 110 and the device head 130.

In an alternative embodiment, the respective positions of the protrusion 160 and the protrusion receiving member 150 are interchanged, i.e. the protrusion 160 is provided in the band 110 with the protrusion receiving member 150 on the device head 130, which is further described herein.

Figure 5:
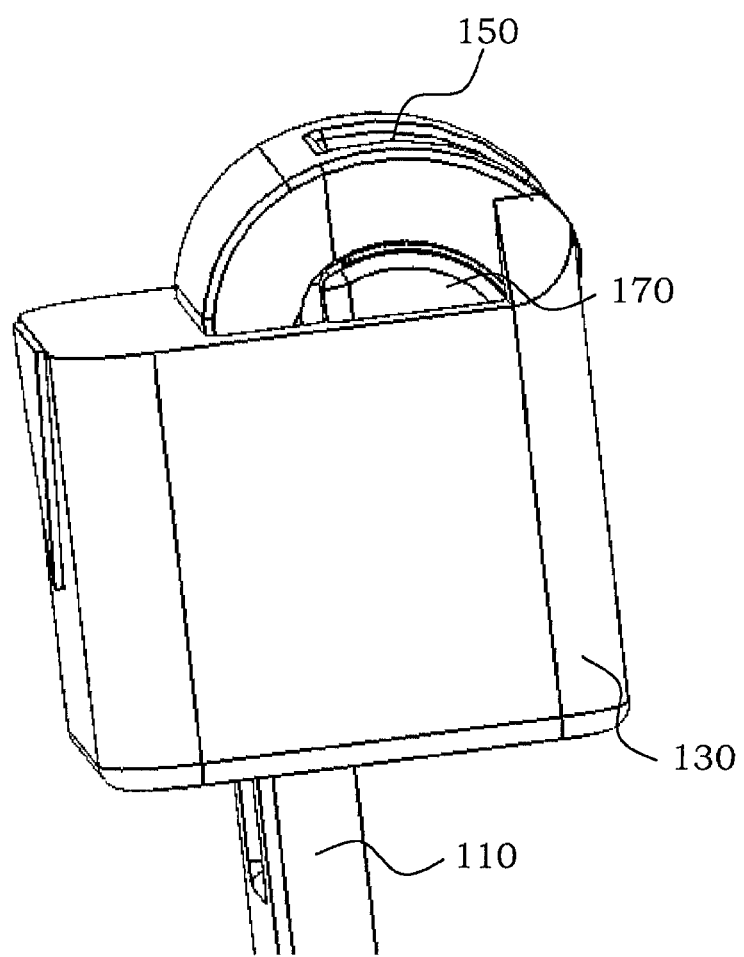
FIG. 5 is a magnification of the device head with the band fully inserted into the head channel.

When the leading end 112 of the band 110 is fed through the channel 135 and is almost fully pulled through the channel 135 to reduce the dimension of the band loop, the protrusion 160 in the head 130 enters the protrusion receiving member 150 in the band 110. Since the protrusion 160 enters the receiving member 160, the band 110 can be further pulled through the channel 135 to even further reduce the band loop diameter. It is actually possible, through the inclusion of the protrusion 160 and the protrusion receiving member 150 of the invention, to reduce the loop diameter to zero and even less than zero or negative. FIG. 5 illustrates the device head 130 with the band 110 inserted into the channel 135 and fully pulled through the channel 135. As is seen in the figure, no loop is present between the band 110 and the head 130 at this position as the protrusion 160 enters the receiving member 150.

This reduction and minimization of loop diameter allows the usage of the medical device 100 even when ligating very thin tissue samples, such as small blood vessels. If the medical device 100 would not have these two matching elements, there would be a (small) loop diameter left even after fully pulling the band 110 to a maximum through the channel 135. However, the protrusion 160 and its matching receiving member 150 allows the band 110 to be fully fed through the channel 135 with no loop diameter left outside of the entrance to the channel 135. Such a solution has not been presented before in the art.

Figure 4:
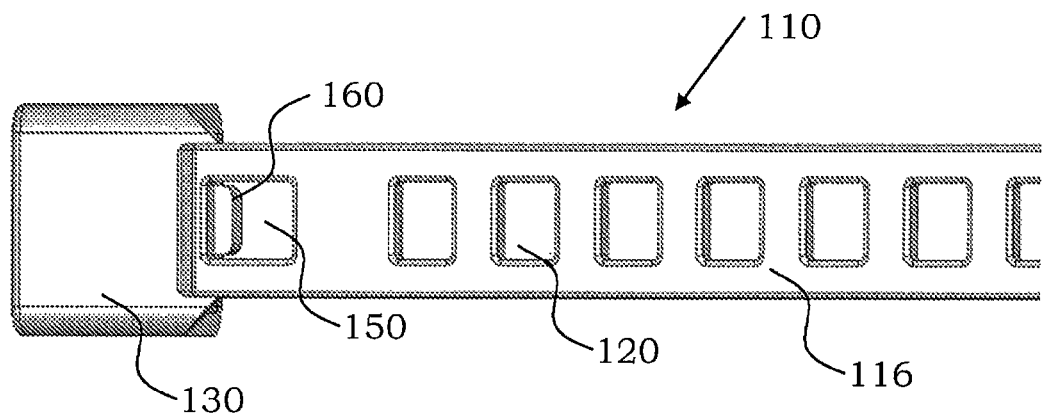
FIG. 4 is a magnification of the back side of the device head and the trailing band portion of the medical device of FIG. 1.

The protrusion receiving member 150 can be realized as an aperture or indentation 150 defined, in an embodiment, in the band 110, where the aperture or indentation 150 has a dimension, i.e. inner circumference, and depth in the case of indentation, which matches the dimension, i.e. outer circumference and height, of the protrusion 160 to allow the protrusion 160 to enter the aperture or indentation 150 when the band 110 is fully or almost fully fed through the channel 135. In the case of an indentation embodiment, the indentation is preferably provided in the front side 118 of the band 110 as illustrated in the figure. The aperture 150 with its matching protrusion is also seen in FIG. 4, which illustrates a backside view of a portion of the medical device 100.

In order to simplify handling of the medical device 100 and in particular simplifying entering the leading band end 112 into the channel 135 in the device head 130 using a single hand, an intermediate portion 115 of the band 110 between the leading end 112 and the trailing end 114 is bent. A preferred embodiment has a U-shaped intermediate portion 115 to position the leading band end 112 close to the device head 130 even when the band 110 has not yet been introduced into the channel 135.

Due to the U-shape of the intermediate band portion 115, a medical person positions the ligating tissue in the space formed between the two, almost parallel, band portions between the trailing end 114 and the intermediate portion 115 and the leading end 112 and the intermediate portion 115. At this position, the person can, using one hand, introduce the leading band end 112 into the channel 135 and pull the band 110 therethrough to start the tissue ligation.

Another preferred embodiment of the present medical device 100 comprises at least one tissue engaging member 170 arranged on the side 132 of the device head 130 comprising the channel entrance. The tissue engaging member 170 is more clearly seen in FIGS. 2 and 3. The member 170 preferably comprises multiple studs or hooks for engaging the tissue as the band 110 is being pulled through the channel 135 to restrict any relative motion and slipping between the tissue and the medical device 100. The tissue gripping or engaging action of the tissue engaging member 170 reduces the risk that the medical device 100 would slide off the tissue during and after ligation, which is a common problem today with (extensive) bleeding as a result. Such ligature sliding according to the prior art during and/or after operation lengthens the operation time and/or requires a new surgical procedure to attach a new ligature around the tissue. Thus, preventing or at least restricting any tissue sliding during and after ligation is an advantageous feature of the medical device 100 of the present invention.

In a preferred embodiment, the tissue engaging member 170 comprises a first tissue engaging member 170A and a second tissue engaging member 170B arranged on opposite sides of the channel 135 on the side of the device head 130 containing the channel entrance. More preferably, the two engaging members 170A, 170B are positioned on the device head 130 to protrude against the front side 118 of the band 110, when the band 110 is fed through the channel 135, as is seen in FIG. 5. This means that the tissue engaging member 170 also helps reduce the band loop diameter to small values, such as zero or even negative diameter. FIG. 5 clearly illustrates how the trailing end 114 of the band 110 aligns around tissue engaging member 170 at this band-feeding stage.

Another advantage of the tissue engaging member 170 is that it squeezes or crushes blood vessels in the tissue during ligation, thereby preventing or at least reducing any bleeding.

In alternative embodiments, the tissue engaging member 170 is not necessarily arranged in the device head 130. In clear contrast, the tissue engaging member 170 is then provided on the band 110, preferably in connection with the trailing end 114. In such a case, the tissue engaging member 170 is typically present on the front side 118 of the band for pressing, when the band 110 is being pulled into the channel 135, the tissue to ligate against the device head 130. Correspondingly, in the case of multiple tissue engaging members 170A, 170B, one or all of these can be present on the band 110. Thus, the invention also encompasses an embodiment having at least tissue engaging member in the device head 130 and at least one tissue engaging member on the band 110.

Figure 6:
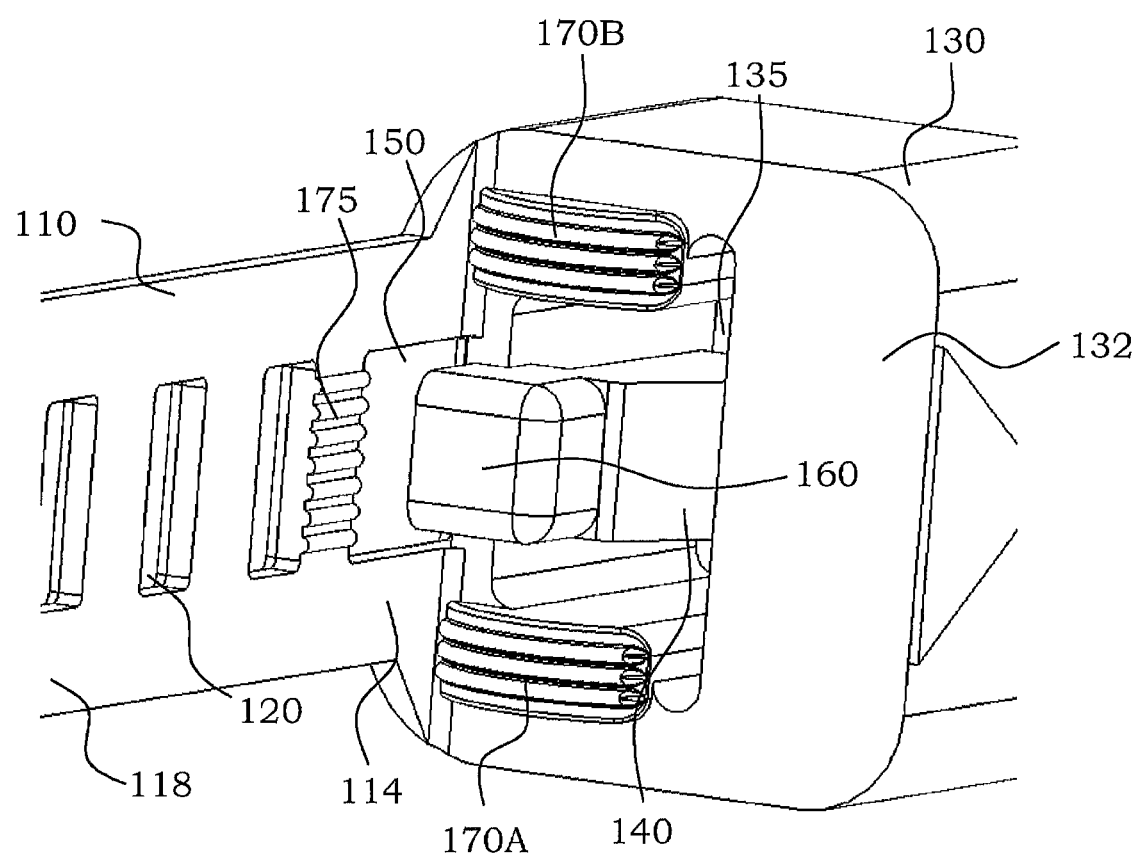
FIG. 6 is a magnification of the device head equipped with tissue engaging member on the band.

FIG. 6 is a magnification of the device head 130 and the trailing band portion 114 of the medical device according to another embodiment. This embodiment is basically similar to the embodiment discussed above in connection with FIG. 3. However, in the present embodiment, a tissue engaging member 175 is provided on the front side 118 of the band 110 in connection with the trailing portion 114 of the band 110. This tissue engaging member 175 is in the form of protrusions extending beyond the general surface of the front side 118. The protrusions may be in the form of ridges as shown in the figure but could alternatively be circular elevations, studs, hooks, or any other tissue engaging structure.

The tissue engaging member 175 can cover substantially the major portion of the front side 118 that is closest to the device head 130 possibly excluding portions of the front side 118 occupied by the ratchet members 120. In the embodiment illustrated in FIG. 6, the tissue engaging member 175 is substantially present on the rungs of the ladder formed by the ratchet member 120 and the portion of the band 110 beyond the rungs. In an alternative approach, the tissue engaging member 175 is only present on the rungs or a portion thereof. A further implementation is to have the tissue engaging member 175 on at least one of the stringers or stiles of the ladder structure up to a certain height from the device head 130.

It is anticipated by the invention that in most applications with rung-implemented tissue engaging member 175, it is generally enough to have the tissue engaging member 175 arranged on the lowest rung as is illustrated in the figure. However, it is indeed possible to have the tissue engaging member 175 also provided on rungs more distance from the device head 130.

The tissue engaging member 175 arranged on the band front side 180 has similar tissue engaging effects as the above-described tissue engaging members 170A, 170B provided in the device head 130. In other words the tissue engaging member 175 reduces the risk that the medical device would slide of the tissue during and after the ligation.

The medical device 100 can be equipped with the band-arranged tissue engaging member 175 as the sole tissue engaging structure. Alternatively, this tissue engaging member 175 is complemented with the one or both tissue engaging members 170A, 170B arranged in the device head 130 as illustrated in the figure. A further embodiment is to only use the head-implemented tissue engaging member(s) 170A, 170B. Still another embodiment of the medical device 100 does not have any dedicated tissue engaging members. However, the design and operation of the protrusion 160 and the protrusion receiving member 150 will together achieve tissue engaging properties.

The medical device 100 of the embodiments basically achieves a double ligation, thereby significantly increasing the chances of successful tissue ligation. Thus, a first ligation operation occurs between the first stringer or stile of the band 110 and the protrusion 160 in combination with the tissue engaging member 170A. A second ligation operation is correspondingly achieved between the second stringer or stile and the protrusion 160 in combination with the tissue engaging member 170B. In practical applications using prior art ligatures, two ligatures are often positioned next to each other on the tissue to ligate for security reasons. Embodiments of the invention relax this need for usage of multiple separate ligatures as the medical device 100 itself can provide two ligations separated a few millimeters from each other, depending on the width of the protrusion 160.

In a preferred embodiment, the device head 130 is integral with and extends from the trailing end 114 of the band 110. The medical device 100 can be moulded to a desired form and size. In most typical implementations, the length of the band 110 could be from about one or few centimeters to one or more decimeters, with a thickness from the range of sub-millimeters to one or more millimeters and a width from the range of sub-millimeters to one or more millimeters. The width of the band 110 must not necessarily be uniform. In clear contrast, the leading end 112 could be narrower than the trailing end 114 to thereby facilitate insertion of the leading end 112 into the head channel 135. Correspondingly, the length of the band portion from the leading end 112 up to the intermediate portion 115 could be somewhat longer than the band portion from the trailing end 114 up to the intermediate portion 115. This prevents the leading end 112 from easily dropping out of the device head 130 once introduced into the channel 135.

The actual size of the medical device 100 is though not decisive for the teachings of the present invention and can instead be selected based on the particular application, animal/human subject and/or tissue to be ligated.

In the embodiments of the medical device discussed above, the protrusion has been arranged in the device head with the protrusion receiving member in the band. The invention is though not limited thereto. In alternative implementations, the protrusion is provided in the band in connection with the trailing end thereof, preferably in the front side of the band. The protrusion receiving member is then arranged in the device head in connection with the band entrance to the channel, preferably on one of the inner walls defining the channel through the device head. These alternative positions of the protrusion and the protrusion receiving member can be applied to any of the above-identified embodiments of the medical device.

The same advantageous tissue ligation with small and even zero loop diameter can be achieved regardless of whether the protrusion is provided on the band with the protrusion receiving member in the device head or with the protrusion arranged in the device head and the protrusion receiving member in the band.

It is anticipated by the invention that the protrusion receiving member, if arranged in the device head, can be in the form of an aperture in one of the head walls. Alternatively and typically more preferred in these embodiments, the protrusion receiving member is in the form of an indentation in the head wall facing the channel and preferably being the head wall that is positioned on the same side of the device head as the band is anchored to the device head. In such a case, the lock member is preferably arranged in or in connection with the opposite inner wall of the device head, i.e. basically on the opposite inner wall than what has been illustrated in FIGS. 1-3 and 6.

The material of the medical device is a biocompatible material, which does not have any major toxic or injurious effects on the animal or human body. Examples of such biocompatible materials include hypoallergenic materials traditionally employed for implantable medical devices. Both plastic and metal (alloy) materials, such as titanium, titanium alloys and stainless steel, can be used as long as the band material is flexible enough to allow being bent when pulling the leading band end through the channel in the device head.

Currently preferred materials are bio-absorbable materials that can be left in the animal or human body and are resorbed by the body following a time after the surgical procedure. Examples of such bio-absorbable materials include glycolide polymers and copolymers, lactide trimethylene, carbonate, lactone, doxane, caprolactone, lactide polymers, such as formed from aliphatic lactone monomers selected from the group consisting of p-dioxanone, trimethylene carbonate, $\epsilon$-caprolactone, $\delta$-valerolactone, $\beta$-butyrolactone, $\epsilon$-decalactone, 2,5-diketomopholine, pivalolactone, $\alpha$-diethylpropiolactone, ethylene carbonate, ethylene oxalate, 3-methyl-1, 4-dioxane-2,5-dione, 3,3-diethyl-1,4-dioxan-2,4-dione, $\gamma$-butyrolactone, 1,4-dioxepan-2-one, 1,5-dioxepan-2-one, 1,4-dioxan-2-one, 6,8-dioxabicycloctane-7-one, and combinations thereof. Further suitable resorbable materials that can be used according to the present invention are described in U.S. Pat. Nos. 4,968,317 and 4,898,186, the teachings of which regarding resorbable, biocompatible materials is hereby incorporated by reference.

The advantage of using a bio-absorbable medical device is that no further surgical procedure is required for removing the medical device after the ligation operation has been completed and the ligated tissue has healed. This saves both costs and suffering from the relevant human or animal patient. Furthermore, non-absorbable devices can cause longterm negative reactions, such as granulomas.

Figure 7:
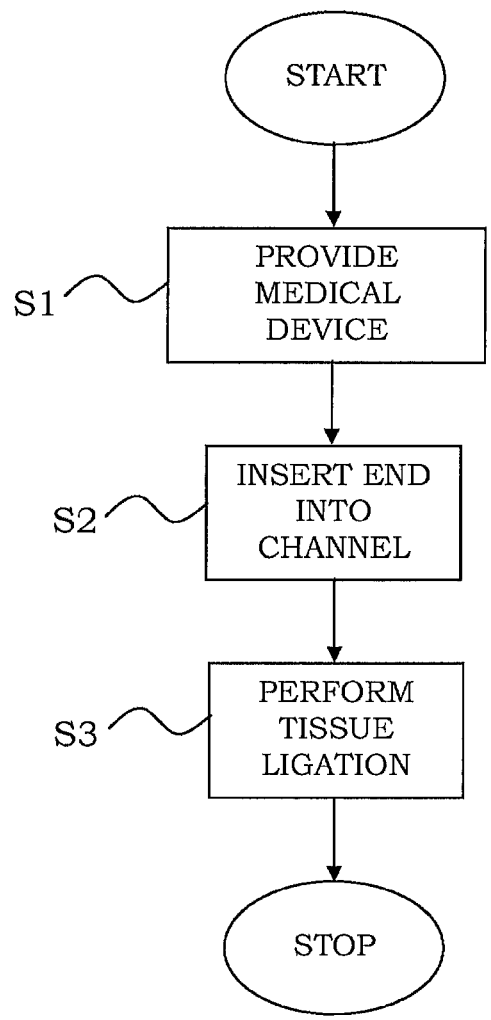
FIG. 7 is a flow diagram of a tissue ligation method according to an embodiment of the present invention.

FIG. 7 is a flow diagram illustrating the use of the medical device of the invention in a tissue ligation method. The method starts in step S1, where a medical device according to the present invention is provided and arranged on a first side of the tissue to be ligated. The leading end of the band is then inserted into the head channel to form a band loop enclosing the tissue in step S2. Due to the preferred U-shaped design of the intermediate band portion, the medical person can easily insert the band end into the channel. Finally, the leading end is pulled through the channel to snare the tissue and achieve a ligation. The design of the medical device allows the leading end to be pulled using a single hand operation, thereby leaving the other hand free from removing surrounding tissue that must not be ligated. Due to the inter-engagement of the ratchet members and the lock member, the band is prevented from reverse movement and opening of the ligation loop. The protrusion and matching protrusion receiving member allows the band to be tightly pulled through the band to minimize the band loop and achieve successful tissue strangulation. The preferred tissue engaging members prevents the medical device from slipping along the tissue before during and after the surgical ligation procedure. If the device is made of a bio-absorbable material, it is gradually dissolved and resorbed, relaxing the need for a further surgical procedure to remove the device from the human or animal body.

It is anticipated by the present invention that any surplus band portion extending beyond the channel exit in the device head after fully pulling the band tight around the tissue can be cut off by the medical person.

The medical device of the invention can be used for ligating vastly varying tissues in both human and animal, preferably mammalian animal bodies. Non-limiting examples include ligation of blood vessels, such as veins and arteries, for instance during laparoscopy; uterine horn; uterine body or testicular funicle, for instance during ovariohysterectomy and castration; during spleen ectomy or intestinal, pulmonary or cardiac procedures. The device can also be used in any soft tissues surgery, in or outside the abdominal or thoracic cavity, where a ligation is desired. The medical device of the present invention can therefore be utilized instead of traditional ligatures but also replace devices such as stapling equipment, ultrasonic scalpels, vessel sealing devices, transfixation ligatures, surgeons knot and other knots, e.g. Miller's knot.

It will be understood by a person skilled in the art that various modifications and changes may be made to the present invention without departure from the scope thereof, which is defined by the appended claims.

The invention claimed is:

1. A medical device for tissue ligation comprising:
    an elongated, flexible band having a front side, a rear side, a leading end and a trailing end, and having ratchet members defined therein;
    a device head connected to said trailing end of said band and having a channel dimensioned for reception of said band;
    a lock member connected to said device head and disposed in connection with said channel and having at least one lock tooth configured to interlock ratchet member defined in said band,
    a protrusion arranged in one of
        i) said device head on a same side relative to said channel as said trailing end, wherein said same side comprises an entrance of said channel in said device head, and said protrusion is arranged in connection with said entrance so that said protrusion is at least partially outside said channel, and
        ii) said band in connection with said trailing end; and
    a protrusion receiving member in the form of an aperture or an indentation arranged in the other of
        i) said device head on said same side relative to said channel as said trailing end, wherein said same side comprises an entrance of said channel in said device head, and said protrusion receiving member is arranged in connection with said entrance so that said protrusion receiving member is at least partially outside said channel, and
        ii) said band in connection with said trailing end,
    said protrusion receiving member being dimensioned for reception of said protrusion.

2. The medical device according to claim 1, wherein said protrusion is arranged in said device head on said same side relative to said channel as said trailing end.

3. The medical device according to claim 2, wherein said lock tooth is configured to interlock said ratchet members defined in said band when said band is fed into said channel and said protrusion receiving member is configured and dimensioned for reception of said protrusion when said band is fed into said channel.

4. The medical device according to claim 1, wherein said protrusion receiving member is provided in said band in an interface between said trailing end and said device head.

5. The medical device according to claim 1, wherein said lock tooth is configured to interlock said ratchet members defined in said band when said band is fed into said channel and said protrusion receiving member is configured and dimensioned for reception of said protrusion when said band is fed into said channel.

6. The medical device according to claim 5, wherein said protrusion receiving member is positioned for reception of said protrusion when said band is fully fed into said channel.

7. The medical device according to claim 1, wherein said protrusion receiving member is an aperture or indentation defined in said band.

8. The medical device according to claim 7, wherein said front side has said ratchet members defined therein.

9. The medical device according to claim 1, wherein an intermediate portion of said band between said leading end and said trailing end is bent.

10. The medical device according to claim 9, wherein said intermediate portion of said band has a general U-shape.

11. The medical device according to claim 1, further comprising at least one tissue engaging member arranged on a side of said device head comprising said band entrance of said channel.

12. The medical device according to claim 11, further comprising
    a first tissue engaging member; and
    a second tissue engaging member, said first and second tissue engaging members being arranged on opposite sides of said channel on said side of said device head comprising said band entrance of said channel.

13. The medical device according to claim 11, wherein said at least one tissue engaging member comprises multiple studs for engagement with a tissue and restricting relative movement between said tissue and said medical device when said band is being fed into said channel.

14. The medical device according to claim 1, wherein said device head being integral with and extending from said trailing end of said band.

15. The medical device according to claim 1, wherein said medical device is made of a bio-absorbable material.

16. The medical device according to claim 1, wherein said lock member and said ratchet member are arranged for inter-engagement to permit forward movement of said band through said channel but restrain the band against reverse movement through said channel.

17. The medical device according to claim 1, wherein said ratchet members comprises an array of holes through said band forming a ladder structure, said locking tooth is arranged for step-by-step protrusion into holes of said array as said band is being fed through said channel.

18. The medical device according to claim 1, further comprising a protruding tissue engaging member arranged on said front side of said band in connection with said trailing end of said band.

19. A tissue ligation method comprising:
    providing a medical device according to claim 1 on a first side of said tissue;
    inserting said leading end of said band into said channel to form a loop of said band around said tissue; and pulling said leading end of said band through said channel to lock said band around said tissue and achieve a tissue ligation.

* * * * *